United States Patent [19]
Peglion et al.

[11] Patent Number: 5,965,575
[45] Date of Patent: Oct. 12, 1999

[54] N-ARYL PIPERIDINE COMPOUNDS AS 5HT$_{1B}$ ANTAGONISTS

[75] Inventors: Jean-Louis Peglion, le Vesinet; Bertrand Goument, Viroflay; Mark Millan, le Pecq; Alain Gobert, Saint Denis; Valérie Audinot, Poissy, all of France

[73] Assignee: Adir Et Compagnie, Courbevoie, France

[21] Appl. No.: 09/049,233

[22] Filed: Mar. 27, 1998

[30] Foreign Application Priority Data

Mar. 27, 1997 [FR] France .................................. 97 03760

[51] Int. Cl.$^6$ ........................ A61K 31/445; C07D 405/12
[52] U.S. Cl. ........................ 514/321; 514/294; 514/319; 514/324; 514/422; 546/94; 546/196; 546/197; 546/202; 546/205; 548/525; 548/526; 548/527
[58] Field of Search .............................. 546/94, 196, 197, 546/202, 205; 514/294, 319, 321, 324, 422; 548/525, 526, 527

[56] References Cited

U.S. PATENT DOCUMENTS 5,767,116  6/1998  Kerrigan et al. .................. 514/212

*Primary Examiner*—Celia Chang
*Attorney, Agent, or Firm*—The Firm of Gordon W. Hueschen

[57] ABSTRACT

New N-arylpiperidine compounds of formula:

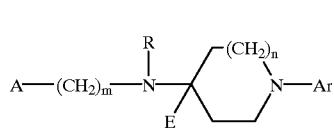

wherein:

A, m, R, E, n and Ar are as defined in the description, the isomers thereof and the addition salts thereof with a pharmaceutically acceptable acid, and medicinal products containing the same are useful in the treatment of disorders involving the serotininergic system.

7 Claims, No Drawings

N-ARYL PIPERIDINE COMPOUNDS AS 5HT$_{1B}$ ANTAGONISTS

FIELD OF THE INVENTION

The present invention relates to new N-arylpiperidine compounds, a process for their preparation and pharmaceutical compositions containing them.

DETAIL DESCRIPTION OF THE INVENTION

More specifically, the present invention relates to N-arylpiperidine compounds of formula I:

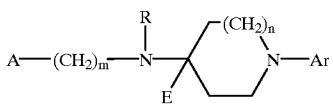

wherein:
  m represents an integer from 1 to 5 inclusive;
  n represents 1 or 2;
  R represents a hydrogen atom, a straight-chain or branched (C$_1$–C$_5$)alkyl radical or an aralkyl radical in which the alkyl moiety contains from 1 to 5 carbon atoms in straight or branched chain;
  E represents a hydrogen atom or a methyl radical;
  Ar represents:

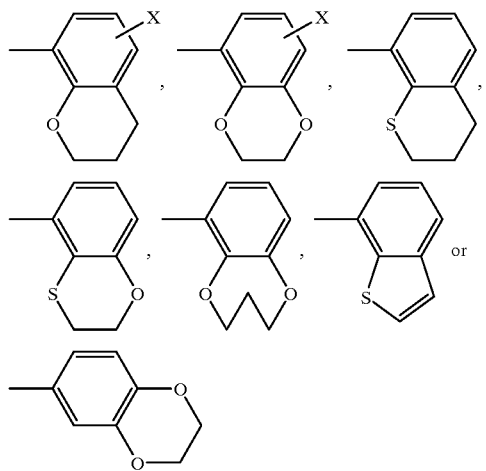

X being a hydrogen or halogen atom
and A represents:

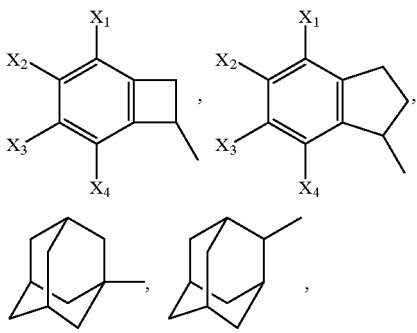

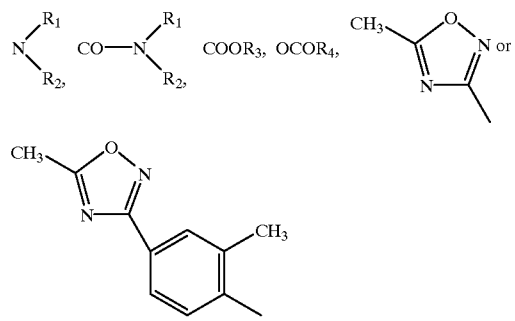

wherein:
  X$_1$, X$_2$, X$_3$ and X$_4$, which may be identical or different, each represents a hydrogen or halogen atom, a (C$_1$–C$_5$) alkyl or (C$_1$–C$_5$)alkoxy radical each of which is straight-chain or branched, a trifluoromethyl, hydroxy, cyano or nitro radical, or radical wherein: R$_1$, R$_2$ and R$_3$, which may be identical or different, each represents a hydrogen atom or a straight-chain or branched (C$_1$–C$_5$)alkyl radical, and R$_4$ represents a straight-chain or branched (C$_1$–C$_5$)alkyl radical, or
  a pair adjacent to one another form, together with the carbon atoms of the phenyl nucleus to which they are bonded, a 5-membered or 6-membered ring composed of atoms selected from the atoms carbon, oxygen, nitrogen and sulphur,
  where they exist in the form of a racemic mixture or in the form of optical isomers,
  and physiologically tolerable acid addition salts thereof.

The products of the present invention may be used as medicaments in the treatment of disorders in which involvement of the serotoninergic system has been demonstrated, such as psychiatric disorders (depression, anxiety, panic attack, schizophrenia, aggression, impulsive disorders, obsessive-compulsive disorders), degenerative diseases (Parkinson's disease, Alzheimer's disease), pain, migraine, headaches, cerebral vascular accidents, bulimia, anorexia, drug abuse and also in cardiovascular disorders (unstable angina) since, like the central nervous system, the serotoninergic system is also present in the cardiovascular areas.

Numerous serotonin receptors have been identified and recently have been cloned. They have been classified into seven major classes, 5-HT$_1$ to 5-HT$_7$, on the basis of their primary structure and their mode of coupling with the transduction systems (cf. F.G. Boess, Molecular Biology of 5-HT Receptors, *Neuropharmacol.*, 1994, 33, 275). Those classes are themselves divided into sub-types. Sub-types 5-$HT_{1A}$, 5-$HT_{1B}$ (formerly 5-$HT_{1D\beta}$) and 5-$HT_{1D}$ (formerly 5-$HT_{1D\alpha}$) are known for the 5-$HT_1$ receptor (for a recent review and discussion of the nomenclature see R. P. Hartig, *Trends in Pharmacol. Sciences*, 1996, 17, 103).

The application of the present invention concerns more especially the 5-$HT_{1B}$ receptor since the products claimed act as powerful and selective ligands of that receptor. 5-$HT_{1B}$ receptors are located post-synaptically in the cerebral region and on the peripheral sympathetic nerve-endings, the cerebral blood vessels and the trigeminal primary afferent nerves (G. J. Molderings, *Naunyn-Schmiedeberg's Arch. Pharmacol.*, 1990. 342, 371; E. Hamel, *Mol. Pharmacol.*, 1993, 44, 242; A. T. Bruinvels, *Eur. J. Pharmacol.*, 1992, 227, 357). Their location implies that, by activation of 5-$HT_{1B}$ receptor populations, it is possible to treat migraines and headaches with agonists by both a vascular and neurogenic effect. With antagonists it will be possible by action on the peripheral receptors to treat disorders of the cardiovascular system, such as unstable angina. In addition, the populations of 5-$HT_{1B}$ receptors, which are also present in high concentrations in the cornu dorsale of the spinal cord, the basal ganglia, the hippocampus and the other limbic structures of the frontal cortex (C. Del Arco, *Naunyn-Schmiedeberg's Arch. Pharmacol.*, 1992, 347, 248; S. Lowther, *Eur. J. Pharmacol.*, 1992, 222, 137; X Langlois, *J. Neurochenm*, 1995, 65, 2671), may be partly responsible for disorders of mood and behaviour and may be involved in the mechanisms of nociception. On the basis of their dual location, on the one hand on the post-synaptic serotoninergic neurons and on the other hand on cell bodies where they assume the role of autoreceptors, their involvement in pathogenesis can easily be deduced, and consequently selective ligands of those receptors may be used in the treatment of depression, anxiety, impulsive disorders and other psychiatric disorders associated with dysfunction of serotoninergic transmission (C. Waeber, *Neurochem. Res.*, 1990. 15, 567; K. Herrick-Davis, *J. Neurochem.*, 1988, 51, 1906).

Concerning the 5-$HT_{1B}$ (ex-5-$HT_{1D\beta}$) receptor, that receptor is predominant in the central nervous system of humans and guinea pigs. Furthermore, only 5-$HT_{1B}$ receptors are located as autoreceptors, which is not true of 5-$HT_{1D}$ (ex-5-$HT_{1D\alpha}$) receptors. 5-$HT_{1B}$/5-$HT_{1D}$ receptor ligands have been described in the Applications WO 96/00720 and WO 96/12713: they are naphthylpiperazine compounds. 5-$HT_{1B}$/5-$HT_{1D}$ receptor antagonists having a biphenyl structure have also been described in the Application WO 96/19477. Those structures in no way suggest the compounds of the present invention. Patent Application WO 95/07274 describes compounds having a 4-aminopiperidine structure used in the treatment of disorders of the central nervous system. In the general formula the extracyclic nitrogen may be bonded by way of an alkane chain to benzodioxane, tetrahydronaphthalene and chroman nuclei. Those structures in no way suggest the structures of the present invention.

The activity of the products of the present invention has been demonstrated in numerous biological and pharmacological tests.

It was possible to evaluate in vitro the selectivity for 5-$HT_{1B}$ receptors by binding experiments, especially by comparison with 5-$HT_{1A}$ receptors.

Using the hypothermia test on the guinea-pig (M. Stingle et al., *J. of Psychopharmacology*, 1994, 8, 14) it was possible to determine the agonist or antagonist nature of the products of the invention.

The microdialysis experiments demonstrate the value of the products of the present invention in the treatment of various pathologies of the central nervous system. Those tests, carried out in the frontal cortex, make it possible in the case where the products cause an increase in the release of serotonin to envisage their use for depression, impulsive disorders and obesity. If they cause a decrease in the release of serotonin they will be beneficial in the treatment of anxiety, panic attacks, sleep problems, cognitive problems and drug abuse. Finally, if they produce an increase in dopamine and/or noradrenalin, they will be beneficial in the treatment of schizophrenia and, as above, in the treatment of depression and cognitive problems.

The present invention relates also to pharmaceutical compositions comprising as active ingredient a compound of formula I or a physiologically tolerable salt thereof, mixed with or in association with one or more appropriate pharmaceutical excipients.

The pharmaceutical compositions so obtained are generally presented in dosage form containing from 0.5 to 25 mg of active ingredient. They may, for example, be in the form of tablets, dragées, gelatin capsules, suppositories or injectable or drinkable solutions, and may be administered by the oral, rectal or parenteral route, depending on the forms employed.

The dosage varies according to the age and weight of the patient, the administration route and associated treatments and ranges from 0.5 to 25 mg of active ingredient from 1 to 3 times per day.

The present invention relates also to a process for the preparation of compounds of formula I which is characterised in that:

a compound of formula II:

(II)

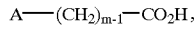

wherein A and m are as defined hereinbefore, is condensed with an amine of formula III:

(III)

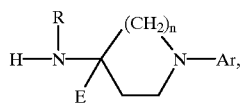

wherein R, E, n and Ar are as defined hereinbefore, by means of carbonyldiimidazole in dichloromethane, to obtain a compound of formula IV:

(IV)

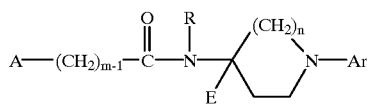

wherein A, m, R, E, n and Ar are as defined hereinbefore, which is reduced to a compound of formula I by means of borane-dimethyl sulphide in tetrahydrofuran.

The compounds of formula I wherein R is as defined hereinbefore with the exception of hydrogen, have also been prepared by converting compounds of formula I wherein R represents a hydrogen atom only (that is to say by conversion of compounds of formula I':

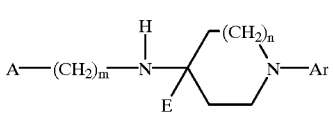 (I')

wherein A, m, E, n and Ar are as defined hereinbefore), by means of conventional alkylation or aralkylation methods using an appropriate halide, tosylate or mesylate of formula V:

RZ  (V)

wherein:
R is as defined hereinbefore and
Z represents a halogen atom selected from the atoms chlorine, bromine and iodine, a tosyloxy radical or a mesyloxy radical.

The compounds of formula III are prepared by the action of a ω,ω'-dihalo-3-aminoalkane of formula VI:

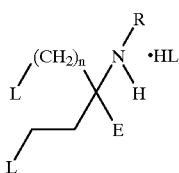 (VI)

wherein L is a chlorine, bromine or iodine atom and R, E and n are as defined hereinbefore with an arylamine of formula VII:

ArNH$_2$  (VII)

wherein Ar is as defined hereinbefore, in a solvent, such as chlorobenzene.

If desired, the optical isomers of compounds of formula I containing one or more asymmetric carbon atoms are prepared according to conventional methods known from the literature.

Salts of compounds of formula I with pharmaceutically acceptable acids were obtained according to conventional methods, as indicated in the Examples hereinbelow.

The starting materials are either known products or are products obtained from known substances in accordance with known procedures, as described hereinbelow in Preparations 1 to 6.

The Examples which follow, given by way of non-limiting example, illustrate the present invention.

The melting points were determined using either a Kofler hot plate (K) or a hot plate under a microscope (MK).

Synthesis of the starting materials

The starting materials used in the following Examples were prepared as follows:

Preparation 1: 1-(2,3-dihydro[1,4]benzodioxin-5-yl)-4-aminopiperidine

Step 1 : 4-hydroxyiminotetrahydro-4H-pyran 40.6 g (0.406 mol) of tetrahydro-4H-pyran-4-one, 118.7 g (1.71 mol) of hydroxylamine hydrochloride and 118.1 g (1.44 mol) of sodium acetate in 810 ml of ethanol are mixed at room temperature. The mixture is heated at reflux for 20 hours and then allowed to cool. The solid is filtered off and rinsed with ethanol and then the filtrates are concentrated. The residue is taken up in 500 ml of ether and stirred vigorously for 2 hours (whitish, very viscous insoluble product). Insoluble material is removed by filtration and the filtrate is concentrated to yield 49.5 g of the desired product (theory: 46.7 g) containing 15% by weight of acetic acid (corrected yield: approximately 90%), which is used as it is.

Step 2: 4-aminotetrahydro-4H-pyran hydrochloride 49.3 g (approximately 0.405 mol) of the compound obtained in the Step 1 are mixed with 15 ml of Raney nickel in 600 ml of ethanol and the mixture is then hydrogenated at room temperature under $5 \times 10^5$ Pa of hydrogen for 4 hours. After filtering off the Raney nickel, 200 ml of 4.1N ethereal hydrogen chloride (approximately 2 eq.) are added, and then the solvents are evaporated off to yield 52.6 g of the desired product (theory: 55.7 g), which is used as it is.

Step 3: 1,5-dibromo-3-aminopentane hydrobromide 52.3 g (380 mmol) of the compound obtained in the above Step are dissolved in 380 ml of fuming hydrobromic acid (60%) at room temperature, then the solution is heated at reflux for 24 hours. It is allowed to cool, then 500 ml of water are added: a solid appears after a few minutes. The whole is cooled in ice, then the solid is filtered off, rinsed with a very small amount of water, then made into a paste again in 200 ml of ether, filtered off, rinsed with ether and dried in vacuo over potassium hydroxide. In that manner, 69.5 g of the desired product (yield: 56%) are obtained in the form of a grey powder.

Step 4: Title product 20 g (59.0 mmol) of the compound obtained in the above Step are mixed with 8.9 g (58.9 mmol) of 5-amino[1,4] benzodioxane in 120 ml of chlorobenzene at room temperature, and the mixture is then heated at reflux overnight. It is allowed to cool: the product is deposited on the walls of the three-necked flask. The chlorobenzene phase is decanted off, and then the residue is taken up in 50 ml of water then 200 ml of N hydrochloric acid, washed with ether (significant emulsion), rendered basic in the cold with concentrated sodium hydroxide solution and extracted 3 times with 200 ml of ethyl acetate each time. The combined organic phases are dried over magnesium sulphate, concentrated (15 g), then chromatographed on silica (eluant: dichloromethane/methanol/ammonium hydroxide, 95/5/0.5) to yield 4.7 g of the desired product (theory: 13.8 g) in the form of a paste.

Preparation 2: 5,6-dihydro-8,9-dimethoxypyrrolo[2,1-a] isoquinol-2-ylacetic acid Step 1: 5,6-dihydro-8,9-dimethoxypyrrolo[2,1-a]isoquinol-2-ylacetic acid methyl ester 10.3 g (50.0 mmol) of 1-methyl-6,7-dimethoxy-3,4-dihydroisoquinoline, 8.3 g (55.0 mmol) of methyl 4-chloroacetoacetate and 12.6 g (150 mmol) of sodium hydrogen carbonate in 100 ml of ethanol are heated at reflux for 5 hours. After evaporation to dryness, the residue is taken up in 250 ml of dichloromethane and washed twice with 100 ml of water each time. After drying the organic phase over magnesium sulphate and then concentrating, the residue (15.5 g) is chromatographed on 500 g of silica (eluant: dichloromethane) to yield 8.5 g of the expected product (theory: 15.1 g).

Step 2: Title product

At room temperature, 17 ml (34 mmol) of 2N sodium hydroxide solution are added dropwise to 8.4 g (27.9 mmol) of the compound obtained in the above Step suspended in 55 ml of methanol and the whole is stirred overnight. After evaporation to dryness, the residue is taken up in 50 ml of water and washed with 50 ml of ether. The aqueous phase is acidified with 50 ml of N hydrochloric acid and extracted twice with 250 ml of dichloromethane each time. The combined organic phases are dried over magnesium sulphate and then concentrated to yield 7.5 g of the desired product (theory: 8.0 g).

M.p. (K)=179° C.

Preparation 3: 5,6-dihydropyrrolo[2,1-a]isoquinol-2-ylacetic acid

Obtained in the same manner as Preparation 2, but using 1-methyl-3,4-dihydroisoquinoline in Step 1.

M.p. (K)=75–85° C.

Preparation 4: 8-chloro-5,6-dihydro-9-methoxypyrrolo[2,1-a]isoquinol-2-ylacetic acid Obtained in the same manner as Preparation 2, but using 1-methyl-6-chloro-7-methoxyiso-quinoline in Step 1.

M.p. (K)=128° C.

Preparation 5: 5,6-dihydro-8,9-dimethoxypyrrolo[2,1-a]isoquinol-2-ylcarboxylic acid Step 1: 5,6-dihydro-8,9-dimethoxypyrrolo[2,1-a]isoquinol-2-ylcarboxylic acid ethyl ester Obtained in the same manner as the product of Step 1 of Preparation 2 but using ethyl bromopyruvate instead of methyl 4-chloroacetoacetate. Purification of the reaction mixture by chromatography on silica using as eluant a $CH_2Cl_2/CH_3COOC_2H_5$ 98/2 mixture yields the expected product in a yield of 77%.

Step 2: Title product

Obtained in the same manner as the product of Step 2 of Preparation 2 but using ethanol as solvent instead of methanol. M.p. (MK): 238–242° C.

Preparation 6: 1-(6-fluorochroman-8-yl)-4-aminopiperidine

Step 1: 6-fluorochroman-8-carboxaldehyde 13.74 g (90.28 mmol) of 6-fluorochroman are dissolved in 250 ml of methylene chloride. The whole is cooled to 0° C. and 20.15 ml (0.18 mol) of $TiCl_4$ are added dropwise. The solution becomes brown and is stirred for 10 minutes at room temperature. 8.78 ml (99.3 mmol) of α,α-dichloromethyl ether are then introduced. The whole is stirred overnight at room temperature, poured into ice-cold water and decanted. The organic phase is dried and evaporated to yield 17.7 g of a residue which is purified by chromatography on silica (eluant $CH_2Cl_2$/cyclohexane: 50/50). 6.3 g of the expected product are obtained. Yield: 38.7%.

Step 2: 6-fluorochroman-8-carboxylic acid

The aldehyde obtained in the above Step is dissolved in 52 ml of acetone. The solution is cooled to 0° C. 17.43 ml of Jones reagent are slowly added while maintaining the temperature below 10° C. The whole is stirred for 4 hours at room temperature, the acetone is evaporated off and the residue is taken up in 60 ml of water and extracted with ether. The ethereal phases are extracted with 1N sodium hydroxide solution. The basic phases are rendered acidic with concentrated hydrochloric acid and extracted with ether. 5.31 g of the expected product are obtained. Yield: 77.5%.

Step 3: Benzyl N-(6-fluorochroman-8-yl)carbamate

A solution composed of 137 ml of toluene, 5.3 g (27.07 mmol) of the acid obtained in the above Step, 4.72 ml of triethylamine and 7.29 ml (33.83 mmol) of diphenylphosphoryl azide are heated at 90° C. for 2 hours. While maintaining that temperature, 3.52 ml of benzyl alcohol are then added and the whole is left at the same temperature for 20 hours, washed with water, 0.5N hydrochloric acid, again with water and then with sodium hydrogen carbonate solution and finally with water. The whole is dried and evaporated to yield 8.2 g of the expected product.

Step 4: 8-amino-6-fluorochroman 8.1 g of the compound obtained in Step 3 are dissolved in 80 ml of ethanol. The solution is hydrogenated at normal pressure and room temperature in the presence of 0.39 g of palladium-on-carbon. Filtration and evaporation yield 4.6 g of a liquid which corresponds to the expected product.

Step 5: Title product 2 g of the compound obtained in the above Step are treated as described in Preparation 1, Step 4. 1.1 g of the desired product are obtained.

EXAMPLE 1

N-[1-(2,3-dihydro[1,4]benzodioxin-5-yl)piperid-4-yl]-N-[2-(indan-1-yl)ethyl]amine and its Hemifumarate Step 1: Acid/amine coupling At room temperature, 0.73 g (4.5 mmol) of carbonyldiimidazole are added in one go to 0.75 g (4.3 mmol) of indan-1-ylacetic acid in 15 ml of dichloromethane, and the mixture is stirred at room temperature for 4 hours. 1.0 g (4.3 mmol) of 1-(2,3-dihydro[1,4]benzodioxin-5-yl)-4-aminopiperidine (described in Preparation 1) dissolved in 5 ml of dichloromethane are then rapidly added and stirring is continued overnight at room temperature. 100 ml of dichloromethane are then added and the whole is washed with 100 ml of N sodium hydroxide solution and 100 ml of water. Drying over magnesium sulphate and concentration yields 1.55 g of the desired product (theory: 1.7 g).

Step 2: Reduction of the amide

At room temperature, 1.12 ml (11.8 mmol) of borane-dimethyl sulphide in 5 ml of tetrahydrofuran are added dropwise to 1.55 g (3.9 mmol) of the compound obtained in the above Step in 15 ml of tetrahydrofuran, and the whole is heated at reflux overnight and then allowed to cool. At room temperature, 7 ml of methanol are added and the whole is again heated at reflux for 1 hour. After evaporation to dryness, the residue is taken up in N sodium hydroxide solution and then extracted with dichloromethane. After drying the combined organic phases over magnesium sulphate and then concentrating, the residue (1.5 g) is chromatographed on 170 g of silica (eluant: dichloromethane/methanol 98/2 to 90/10) to yield 0.93 g of the expected product in the form of the free base.

The hemi-fumarate is obtained in ethanol by the addition of one equivalent of 2% fumaric acid in ethanol. Filtration and drying, followed by recrystallisation from ethanol, yield 0.41 g of the expected product. M.p. (K): 189–192° C.

EXAMPLE 2

N-[1-(2,3-dihydro[1,4]benzodioxin-5-yl)piperid-4-yl]-N-(indan-1-yl-methyl)amine and its Fumarate Prepared in the same manner as the product of Example 1, but using indan-1-ylcarboxylic acid instead of indan-1-ylacetic acid in Step 1.

The fumarate of the title product is obtained as described above.

M.p. (MK)=217–220° C.

EXAMPLE 3

N-[1-(2,3-dihydro[1,4]benzodioxin-5-yl)piperid-4-yl]-N-[3-(indan-1-yl)-propyl]amine and its Fumarate Prepared in the same manner as the product of Example 1, but using 3-(indan-1-yl)propionic acid instead of indan-1-ylacetic acid in Step 1.

The fumarate of the title product is obtained as described in Step 2 of Example 1.
M.p. (MK)=199–202° C.

EXAMPLE 4

N-(benzocyclobuten-1-ylmethyl)-N-[1-(2,3-dihydro[1,4]benzodioxin-5-yl)piperid-4-yl]amine and its Fumarate Prepared in the same manner as the product of Example 1, but using benzocyclobuten-1-yl-carboxylic acid instead of indan-1-ylacetic acid in Step 1.
The fumarate is obtained as described in Step 2 of Example 1.
M.p. (MK)=224–226° C.

EXAMPLE 5

N-[3-(benzocyclobuten-1-yl)propyl]-N-[1-(2,3-dihydro[1,4]benzodioxin-5-yl)piperid-4-yl]amine and its Fumarate Prepared in the same manner as the product of Example 1, but using 3-(benzocyclobuten-1-yl)propionic acid instead of indan-1-ylacetic acid in Step 1.
The fumarate is obtained as described in Step 2 of Example 1.
M.p. (MK)=178–180° C.

EXAMPLE 6

N-[2-(benzocyclobuten-1-yl)ethyl]-N-[1-(2,3-dihydro[1,4]benzodioxin-5-yl)piperid-4-yl]amine and its Fumarate Prepared in the same manner as the product of Example 1, but using benzocyclobuten-1-ylacetic acid instead of indan-1-ylacetic acid in Step 1.
The fumarate is prepared as described in Step 2 of Example 1.
M.p. (MK)=186–188° C.

EXAMPLE 7

N-[4-(benzocyclobuten-1-yl)butyl]-N-[1-(2,3-dihydro[1,4]benzodioxin-5-yl)piperid-4-yl]amine and its Fumarate Prepared in the same manner as the product of Example 1, but using 4-(benzocyclobuten-1-yl)butyric acid instead of indan-1-ylacetic acid in Step 1.
The fumarate is obtained as described in Step 2 of Example 1.
M.p. (MK)=201–205° C.

EXAMPLE 8

N-[1-(2,3-dihydro[1,4]benzodioxin-5-yl)piperid-4-yl]-N-(4,5-dimethoxybenzocyclobuten-1-ylmethyl)amine and its Fumarate Prepared in the same manner as the product of Example 1, but using 4,5-dimethoxybenzocyclobuten-1-ylcarboxylic acid instead of indan-1-ylacetic acid in Step 1.
The fumarate is obtained as described in Step 2 of Example 1.
M.p. (MK)=218–222° C.

EXAMPLE 9

N-[2-(adamant-1-yl)ethyl]-N-[1-(2,3-dihydro[1,4]benzodioxin-5-yl)-piperid-4-yl]amine and its Fumarate Prepared as described in Example 1, but using adamant-1-ylacetic acid instead of indan-1-ylacetic acid in Step 1.
The fumarate is obtained as described in Step 2 of Example 1.
M.p. (MK)=251–254° C.

EXAMPLE 10

N-[adamant-1-ylmethyl)-N-[1-(2,3-dihydro[1,4]benzodioxin-5-yl)-piperid-4-yl]amine and its Fumarate Prepared as described in Example 1, but using adamant-1-ylcarboxylic acid instead of indan-1-ylacetic acid in Step 1.
The fumarate is obtained as described in Step 2 of Example 1.
M.p. (MK)=239–243° C.

EXAMPLE 11

5,6-dihydro-8,9-dimethoxy-2-{2-{[1-(2,3-dihydro[1,4]benzodioxin-5-yl)-piperid-4-ylamino]ethyl}}pyrrolo[2,1-a]isoquinoline and its Hemi-fumarate Prepared as described in Example 1, but using 5,6-dihydro-8,9-dimethoxypyrrolo[2,1-a]isoquinol-2-ylacetic acid (Preparation 4) instead of indan-1-ylacetic acid in Step 1.
The hemi-fumarate is obtained as described in Step 2 of Example 1.
M.p. (MK)=208–213° C.

EXAMPLE 12

5,6-dihydro-2-{2-{[1-(2,3-dihydro[1,4]benzodioxin-5-yl)piperid-4-ylamino]ethyl}}pyrrolo[2,1-a]isoquinoline and its Hemi-fumarate Prepared as described in Example 1, but using 5,6-dihydropyrrolo[2,1-a]isoquinol-2-ylacetic acid (Preparation 3) instead of indan-1-ylacetic acid in Step 1.
The hemi-fumarate is obtained according to the method in Step 2 of Example 1.
M.p. (MK)=221–225° C.

EXAMPLE 13

5,6-dihydro-9-methoxy-2-{2-{[1-(2,3-dihydro[1,4]benzodioxin-5-yl)piperid-4-ylamino]ethyl}}pyrrolo[2,1-a]isoquinoline and its Hemi-fumarate Prepared as described in Example 1, but using 8-chloro-5,6-dihydro-9-methoxypyrrolo[2,1-a]-isoquinol-2-ylacetic acid (Preparation 4) instead of indan-1-ylacetic acid in Step 1.
The hemi-fumarate is obtained according to the method in Step 2 of Example 1.
M.p. (MK)=252–255° C.

EXAMPLE 14

1-(2,3-dihydro[1,4]benzodioxin-5-yl)-4-{N-benzyl-2-(indan-1-yl)ethylamino}piperidine and its Fumarate At room temperature, 1.0 g (2.6 mmol) of the free base of the product obtained in Example 1, Step 2, 0.31 ml (2.6 mmol) of benzyl bromide, 1.46 g (10.6 mmol) of potassium carbonate and 30 ml of acetone are mixed together. The mixture is heated at reflux for 24 hours and then evaporated to dryness, and the residue is taken up in 100 ml of ethyl acetate and washed twice with 50 ml of water each time. Drying over magnesium sulphate and concentration yield 1.23 g of the expected product in the form of the free base. The corresponding fumarate is obtained in ethanol by the addition of one equivalent of a 2% solution of fumaric acid in ethanol. Filtration and drying yield 0.99 g of the expected product.

M.p. (K): 125–128° C.

EXAMPLE 15

5,6-dihydro-8,9-dimethoxy-2-{[1-(2,3-dihydro[1,4]benzodioxin-5-yl)piperid-4-ylamino]methyl}pyrrolo[2,1-a]isoquinoline and its Hemi-fumarate The title product in the form of the base was prepared as described in Example 1, but using 5,6-dihydro-8,9-dimethoxypyrrolo[2,1-a]isoquinol-2-ylcarboxylic acid (described in Preparation 5) instead of indan-1-ylacetic acid in Step 1.
The corresponding hemi-fumarate was obtained as described in Step 2 of Example 1.

M.p. (MK): 244–246° C.

EXAMPLE 16

N-[2-(adamant-2-yl)ethyl]-N-[1-(2,3-dihydro[1,4]benzodioxin-5-yl)piperid-4-yl]amine and its Fumarate The title product in the form of the base was prepared as described in Example 1, but using adamant-2-ylacetic acid instead of indan-1-ylacetic acid in Step 1.
The corresponding fumarate was obtained as described in Step 2 of Example 1. M.p. (MK): 226–230° C.

EXAMPLE 17

N-[2-(adamant-2-yl)ethyl]-N-[1-(chroman-8-yl)piperid-4-yl]amine and its Fumarate The title product in the form of the base was prepared as described in Example 1, but using 1-(chroman-8-yl)-4-aminopiperidine instead of 1-(2,3-dihydro[1,4]benzodioxin-5-yl)-4-amino-piperidine and adamant-2-ylacetic acid instead of indan-1-ylacetic acid in Step 1.
The corresponding fumarate was obtained as described in Step 2 of Example 1. M.p. (MK): 252–256° C.

EXAMPLE 18

5,6-dihydro-8,9-dimethoxy-2-{2-[1-(chroman-8-yl)piperid-4-ylamino]-ethyl}pyrrolo[2,1-a]isoquinoline and its Hemi-fumarate The title product in the form of the base was prepared as described in Example 1, but using 1-(chroman-8-yl)-4-aminopiperidine instead of the compound of Preparation 1 and 5,6-dihydro-8,9-dimethoxypyrrolo[2,1-a]isoquinol-2-ylacetic acid instead of indan-1-ylacetic acid in Step 1.
The corresponding hemi-fumarate was obtained as described in Step 2 of Example 1.

M.p. (MK): 231–235° C.

EXAMPLE 19

5,6-dihydro-8,9-dimethoxy-2-{2-[1-(6-fluorochroman-8-yl)piperid-4-ylamino]ethyl}pyrrolo[2,1-a]isoquinoline and its Hemi-fumarate.

The title product in the form of the base was prepared as described in Example 1, but using 1-(6-fluorochroman-8-yl)-4-aminopiperidine (described in Preparation 6) instead of the compound of Preparation 1 and 5,6-dihydro-8,9-dimethoxypyrrolo[2,1-a]isoquinol-2-ylacetic acid instead of indan-1-ylacetic acid in Step 1.
The corresponding fumarate was obtained as described in Step 2 of Example 1.

M.p. (MK): 215–218° C.

EXAMPLE 20

PHARMCOLOGICAL STUDY

Binding studies
5-$HT_{1B}$ binding
a) Preparation of the membranes

After dissection of guinea-pig brains, the extracted striata are frozen and then homogenised in 20 volumes (weight/volume) of 50 mM tris-HCl (pH 7.7 at room temperature) containing 4 mM $CaCl_2$ and 0.1% ascorbic acid, and centrifuged at 48,000 g for 25 minutes at 4° C. The supernatant is separated and the precipitate is resuspended in the same volume of buffer before being incubated at 37° C. for 15 minutes in order to extract the endogenous serotonin. Finally, the suspension is centrifuged at 48,000 g for 25 minutes at 4° C. and the precipitate is resuspended in 80 volumes of buffer containing 10 $\mu$M pargyline.

b) Binding study

The binding studies ([$^3$H]-GR 125743) are carried out in triplicate in the following buffer: 50 mM tris-HCl (pH 7.7 at room temperature) containing 4 mM $CaCl_2$, 0.1% ascorbic acid and 10 $\mu$M pargyline. The final volume of 500 $\mu$l is formed by 100 $\mu$l of radioligand, 100 $\mu$l of buffer or compound to be tested and 300 $\mu$l of membranes. The serotonin (10 $\mu$M) is used to define the non-specific binding. In the competition experiments, the concentration of [$^3$H]-GR 125743 is 1 nM. The incubations are started by the addition of the membrane preparation and continue for 60 minutes at room temperature. The reaction is stopped by rapid filtration across Whatman GF/B filters pretreated with 0.1% polyethyleneimine, followed by three rinses with cold buffer. The specific binding represents approximately 90% of the total binding at concentrations of radioligand approaching the Kd value.

Analysis of the data

The data are analysed by non-linear regression using the PRISM programme (Graphpad Software Inc., San Diego, Calif.) in order to determine the Kd values (dissociation constant of the radioligand), the Bmax values (maximum number of sites) for the saturation experiments and the $IC_{50}$ values (50% inhibiting concentration) and the Hill number for the competition experiments. The inhibition constant ($K_i$) is calculated according to the Cheng-Prussof equation: $K_i = IC_{50}/1 + L/K_d$ wherein L represents the concentration of the radioligand. The results are expressed as $pK_i = -\log K_i$.

The compounds of the present invention demonstrate a very good affinity for the 5-$HT_{1B}$ receptor. By way of example, the $pK_i$ of the compound of Example 9 is 8.0.

5-$HT_{1A}$ binding

The 5-$HT_{1A}$ receptor binding studies were carried out according to methods known and described in the literature (cf. S. J. Peroutka, *J. Neurochem*, 1986, 47, 529–40, M. J. Millan, *J. Pharmacol. Exp. Ther.*, 1994, 268, 337–52). The results are also expressed as $pK_i$.

The compounds of the present invention have a very low affinity for the 5-$HT_{1A}$ receptor. By way of example the $pK_i$ of the compound of Example 4 is 5.5.

This demonstrates the excellent selectivity of the products of the invention.

Hypothermia test in the guinea-pig

The guinea-pigs are kept in batteries of three, with free access to food and water, for one week before entering the study. One hour before each experiment, the guinea-pigs are placed in individual cages with free access to water. They are put back in their respective batteries at the end of each experiment. The temperature measurements are carried out using a digital thermometer and a rectal probe. Each guinea-pig is weighed, its base body temperature is taken and then the compound of the present invention to be evaluated is injected i.p. or p.o.

In the case of an agonist, the body temperature of each guinea-pig is taken every 30 minutes for 2 hours.

In the case of an antagonist, 15 minutes after injection each guinea-pig is injected again i.p. with the prototype agonist 5-$HT_{1B}$: GR46611 (5 mg/kg/ml). The temperature is then taken every 30 minutes for 2 hours.

The criterion used for evaluation is the difference in temperature at a given time in relation to the base temperature. For each dose of product and for each time ($t_{30}$, $t_{60}$, $t_{90}$, $t_{120}$) the mean and the standard error of the mean are calculated.

By way of example, and to illustrate the effects of the products of the invention at $t_{90}$ and $t_{120}$ and by the i.p. route, the results of the compound of Example 11, which acts as an antagonist, are listed in the following Table.

| INJECTION 1 (a) | INJECTION 2 (b) | ΔT ° C. (90 min)(b) | ΔT ° C. (120 min)(b) |
|---|---|---|---|
| Vehicle | Vehicle | 0 ± 0.1 | 0 ± 0.1 |
| Vehicle | GR46611 (5 mg/kg) | −1.05 ± 0.13 | −1.40 ± 0.36 |
| Product of Example 11 0.04 mg/kg | GR46611 (5 mg/kg) | −1.10 ± 0.36 | −1.43 ± 0.24 |
| Product of Example 11 0.16 mg/kg | GR46611 (5 mg/kg) | −0.57 ± 0.17 | −0.67 ± 0.28 |
| Product of Example 11 0.63 mg/kg | GR46611 (5 mg/kg) | −0.37* ± 0.14 | 0.50* ± 0.18 |

(a): i.p. route
(b): the values are the means ± s.e.m. N ≧ 6 per value
*: P < 0.05 versus vehicle/GR 46611 according to the Dunnett test Microdialysis experiment in rats The rats are anaesthetised with pentobarbital (60 mg/kg i.p.). They are placed in a Kopf stereotaxic apparatus and the cannula guide is implanted in the frontal cortex cingulum in accordance with the coordinates described as follows in the Paxinos and Watson atlas (1982): AP: +2.2, L: ±0.6, DV: −0.2. The rats are placed in separate cages and are not used for dialysis until 5 days later. On the day of dialysis, the probe is slowly inserted and maintained in its position. The probe is perfused at a rate of flow of 1 ml/min. with a solution of 147.2 mM NaCl, 4 mM KCl and 2.3 mM $CaCl_2$ adjusted to pH 7.3 with a phosphate buffer (0.1M). Two hours after implantation, samples are collected every 20 minutes for 4 hours. Three base samples are collected before the administration of the products to be tested. The rats are left in their individual cages for the entire experiment. At the end of the experiment the rats are decapitated and the removed brain is frozen in isopentane. Sections 100 μm thick are cut and stained with cresyl violet, allowing verification of the location of the probes.

Simultaneous quantification of dopamine, norepinephrine and serotonin is carried out as follows: 20 μl of dialysis samples are diluted with 20 μl of mobile phase ($NaH_2PO_4$: 75 mM, EDTA: 20 μM, sodium dodecanesulphonate: 1 mM, methanol: 17.5%, triethylamine: 0.01%, pH: 5.70) and 33 μl are analysed by HPLC with an inverse phase column (Hypersil ODS 5 μm, C18, 150×4.6 mm, Thermo Separation Products, Les Ulis, France) thermo-statically controlled at 45° C. and quantified by way of a coulometric detector. The potential of the first electrode of the detector is fixed at −90 mV (reduction) and the second at +280 mV (oxidation). The mobile phase is injected with a Beckman 116 pump at a rate of flow of 2 ml/min. The sensitivity limits for dopamine, norepinephrine and serotonin are 0.55 fmol per sample. All of the products of the invention are injected by the subcutaneous route in a volume of 1.0 ml/kg. The products are dissolved in distilled water to which a few drops of lactic acid are added if necessary. The quantities of neurotransmitters are expressed as a function of the mean of the three base values. A variance analysis, with the time factor as repeated measurement, followed by a Newman-Keuls test (P<0.05) is used for the statistical evaluation of the effects of the products.

In the case of the agonists a decrease in the extracellular concentration of serotonin was observed.

In the case of the antagonists, reversion of the decrease in the extracellular concentration of serotonin produced by the agonist GR46611 injected 20 minutes after the compounds of the invention to be tested was observed.

We claim:

1. N-arylpiperidine compounds selected from those of formula I:

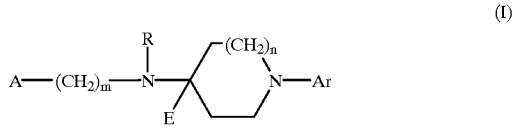

wherein:

m represents 1 to 5 inclusive;

n represents 1 or 2;

R represents hydrogen, straight-chain or branched ($C_1$–$C_5$)alkyl, or aralkyl in which the alkyl moiety contains 1 to 5 carbon atoms inclusive in straight or branched chain;

E represents hydrogen or methyl;

Ar represents:

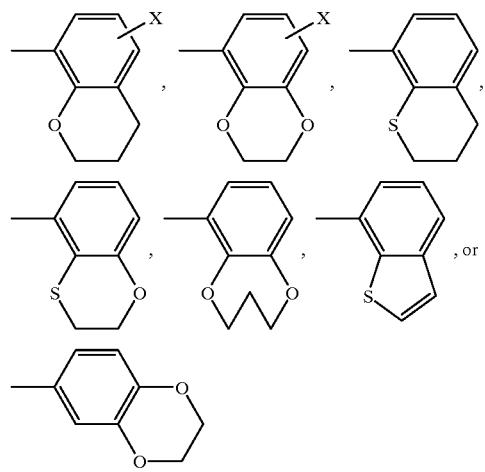

X being hydrogen or halogen and A represents:

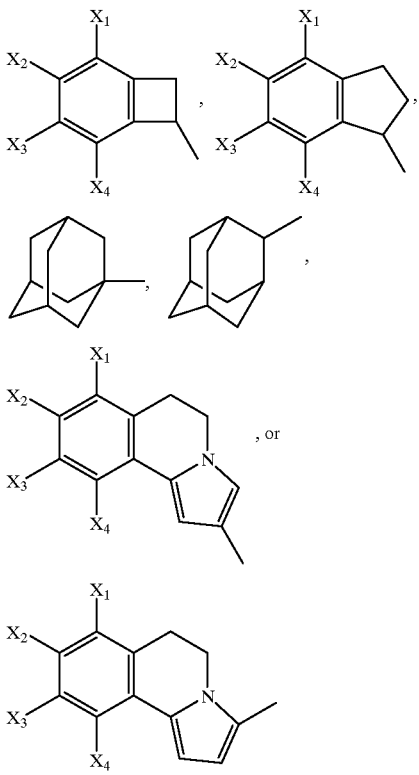

wherein:
$X_1$, $X_2$, $X_3$, and $X_4$, which may be identical or different, each represents hydrogen or halogen, $(C_1-C_5)$alkyl, or $(C_1-C_5)$alkoxy, each of which is straight-chain or branched, trifluoromethyl, hydroxy, cyano, or nitro, or

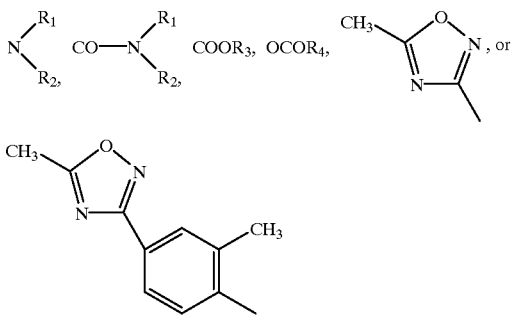

wherein : $R_1$, $R_2$, and $R_3$, which may be identical or different, each represents hydrogen or straight-chain or branched $(C_1-C_5)$alkyl, and $R_4$ represents a straight-chain or branched $(C_1-C_5)$alkyl, or a pair of $X_1$, $X_2$, $X_3$, and $X_4$ adjacent to one another form, together with the carbon of the phenyl to which they are bonded, a 5-membered or 6-membered ring comprising atoms selected from carbon, oxygen, nitrogen, and sulphur, where they exist in the form of a racemic mixture or in the form of optical isomers, and physiologically-tolerable acid addition salts thereof.

2. A compound of claim 1 selected from the group consisting of

N-[1-(2,3-dihydro[1,4]benzodioxin-5-yl)piperid-4-yl]-N-[2-(indan-1-yl)ethyl]amine and its hemi-fumarate,
N-[1-(2,3-dihydro[1,4]benzodioxin-5-yl)piperid-4-yl]-N-(indan-1-ylmethyl)amine and its fumarate,
N-[1-(2,3-dihydro[1,4]benzodioxin-5-yl)piperid-4-yl]-N-[3-(indan-1-yl)propyl]amine and its fumarate,
N-(benzocyclobuten-1-ylmethyl)-N-[1-(2,3-dihydro[1,4]benzodioxin-5-yl)piperid-4-yl]amine and its fumarate,
N-[3-(benzocyclobuten-1-yl)propyl]-N-[1-(2,3-dihydro[1,4]benzodioxin-5-yl)piperid-4-yl]-amine and its fumarate,
N-[2-(benzocyclobuten-1-yl)ethyl]-N-[1-(2,3-dihydro[1,4]benzodioxin-5-yl)piperid-4-yl]-amine and its fumarate,
N-[4-(benzocyclobuten-1-yl)butyl]-N-[1-(2,3-dihydro[1,4]benzodioxin-5-yl)piperid-4-yl]-amine and its fumarate,
N-[1-(2,3-dihydro[1,4]benzodioxin-5-yl)piperid-4-yl]-N-(4,5-dimethoxybenzocyclobuten-1-ylmethyl)amine and its fumarate,
N-[2-(adamant-1-yl)ethyl]-N-[1-(2,3-dihydro[1,4]benzodioxin-5-yl)piperid-4-yl]amine and its fumarate,
N-[adamant-1-ylmethyl)-N-[1-(2,3-dihydro[1,4]benzodioxin-5-yl)piperid-4-yl]amine and its fumarate,
5,6-dihydro-8,9-dimethoxy-2-{2-{[1-(2,3-dihydro[1,4]benzodioxin-5-yl)piperid-4-ylamino]-ethyl}}pyrrolo[2,1-a]isoquinoline and its hemi-fumarate,
5,6-dihydro-2-{2-{[1-(2,3-dihydro[1,4]benzodioxin-5-yl)piperid-4-ylamino]ethyl}}pyrrolo-[2,1-a]isoquinoline and its hemi-fumarate,
5,6-dihydro-9-methoxy-2-{2-{[1-(2,3-dihydro[1,4]benzodioxin-5-yl)piperid-4-ylamino]-ethyl}}pyrrolo[2,1-a]isoquinoline and its hemi-fumarate,
1-(2,3-dihydro[1,4]benzodioxin-5-yl)-4-{N-benzyl-2-(indan-1-yl)ethylamino}piperidine and its fumarate,
5,6-dihydro-8,9-dimethoxy-2-{[1-(2,3-dihydro[1,4]benzodioxin-5-yl)piperid-4-ylamino]-methyl}pyrrolo[2,1-a]isoquinoline and its hemi-fumarate,
N-[2-(adamant-2-yl)ethyl]-N-[1-(2,3-dihydro[1,4]benzodioxin-5-yl)piperid-4-yl]amine and its fumarate,
N-[2-(adamant-2-yl)ethyl]-N-[1-(chroman-8-yl)piperid-4-yl]amine and its fumarate,
5,6-dihydro-8,9-dimethoxy-2-{2-[1-(chroman-8-yl)piperid-4-ylamino]ethyl}pyrrolo[2,1-a]isoquinoline and its hemi-fumarate, and
5,6-dihydro-8,9-dimethoxy-2-{2-[1-(6-fluorochroman-8-yl)piperid-4-ylamino]ethyl}pyrrolo-[2,1-a]isoquinoline and its hemi-fumarate.

3. A compound according to claim 1 which is N-(benzocyclobuten-1-ylmethyl)-N-[1-(2,3-dihydro[1,4]benzodioxin-5-yl)piperid-4-yl]amine or its fumarate.

4. A compound according to claim 1 which is N-[2-(adamant-1-yl)ethyl]-N-[1-(2,3-dihydro[1,4]benzodioxin-5-yl)piperid-4-yl]amine or its fumarate.

5. A compound according to claim 1 which is 5,6-dihydro-8,9-dimethoxy-2-{2-{[1-(2,3-dihydro[1,4]benzodioxin-5-yl)piperid-4-ylamino]ethyl}}pyrrolo[2,1-a]isoquinoline or its hemi-fumarate.

6. A method for treating a living body afflicted with a condition selected from psychiatric disorders, degenerative diseases, pain, migraine, headaches, cerebral vascular accidents, bulimia, anorexia, drug abuse, and cardiovascular disorders comprising the step of administering to the living body a $5HT_{1B}$ antagonistic effective amount of a compound of claim 1, which is effective for alleviation of said condition.

7. A pharmaceutical composition useful in the treatment of disorders involving the serotoninergic system comprising as active principle a $5HT_{1B}$ antagonistic effective amount of a compound as claimed in claim 1, together with one or more pharmaceutically-acceptable excipients or vehicles.

* * * * *